United States Patent [19]

Vlattas

[11] Patent Number: 4,595,535

[45] Date of Patent: Jun. 17, 1986

[54] DIAZACYCLOALKYL-1,2,4-TRIAZOLO[2,3-C][1,3]BENZODIAZEPINES USEFUL AS NEUROLEPTIC AND/OR ANTIHISTAMINIC AGENTS

[75] Inventor: Isidoros Vlattas, Summit, N.J.

[73] Assignee: Ciba-Geigy Corporation, Ardsley, N.Y.

[21] Appl. No.: 643,136

[22] Filed: Aug. 22, 1984

Related U.S. Application Data

[63] Continuation-in-part of Ser. No. 501,328, Jun. 6, 1983, abandoned.

[51] Int. Cl.$^4$ ............... C07D 487/16; A61K 31/495
[52] U.S. Cl. ............... 260/243.3; 260/245.5; 514/220; 514/254; 514/383; 514/384; 544/366; 548/262
[58] Field of Search ............... 260/243.3, 245.5; 514/220

[56] References Cited

U.S. PATENT DOCUMENTS

| | | | |
|---|---|---|---|
| 3,539,573 | 11/1970 | Schmutz et al. | 260/330.3 |
| 4,076,823 | 2/1978 | Wade et al. | 260/465 R |
| 4,192,803 | 3/1980 | Wright, Jr. et al. | 260/243.3 |
| 4,431,589 | 2/1984 | Chakrabarti et al. | 544/366 |
| 4,460,587 | 7/1984 | Vlattas | 514/220 |
| 4,495,101 | 1/1985 | Klaubert et al. | 260/239.3 T |

FOREIGN PATENT DOCUMENTS

81461 6/1983 European Pat. Off.
2077727 6/1981 United Kingdom.

OTHER PUBLICATIONS

Hester et al., Chem. Abstr. 92, 212v (1980).
Hester et al., Chem. Abstr. 91, 91607w (1979).
Kentaro et al., Chem. Abstr. 92, 111072u (1980).
Hester et al., Chem. Abstr. 93, 168239d (1980).
Hester et al., Chem. Abstr. 93 114471e (1980).
Hirai et al., Chem. Abstr. 92 94447a (1980).
Vlattas, Chem. Abst. 101: 211186g.

Primary Examiner—Donald G. Daus
Assistant Examiner—C. Shen
Attorney, Agent, or Firm—Norbert Gruenfeld

[57] ABSTRACT

Described are 5-diazacycloalkyltriazolo[2,3-c][1,3]benzodiazepines, for example compounds of the formula

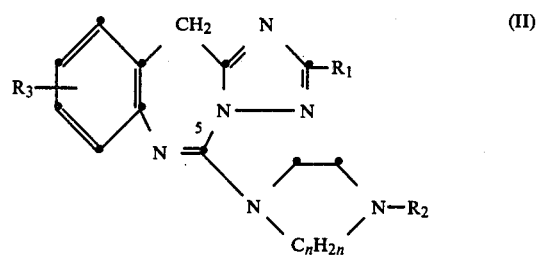

(II)

wherein $R_1$ represents hydrogen, halogen, trifluoromethyl, lower alkylthio, lower alkoxy or lower alkyl; $R_2$ represents hydrogen, lower alkyl or hydroxy-$C_2$–$C_7$ alkyl wherein the hydroxy group is separated from the nitrogen atom by at least 2 carbon atoms; $R_3$ represents hydrogen, lower alkyl, lower alkoxy, lower alkylthio, halogen or trifluoromethyl; and $C_nH_{2n}$ represents ethylene. The synthesis, pharmaceutical compositions and methods of use as neuroleptic and/or antihistaminic agents are given.

11 Claims, No Drawings

DIAZACYCLOALKYL-1,2,4-TRIAZOLO[2,3-C][1,3]BENZODIAZEPINES USEFUL AS NEUROLEPTIC AND/OR ANTIHISTAMINIC AGENTS

CROSS-REFERENCE TO RELATED APPLICATION

This is a continuation-in-part of application Ser. No. 501,328 filed June 6, 1983, now abandoned.

BACKGROUND OF THE INVENTION

Piperazinyl substituted ring fused benzodiazepines have been reported as antipsychotic/neuroleptic agents, e.g., clozapine (U.S. Pat. No. 3,539,573) and 11-piperazinyl-5H-pyrrolo[2,1-c][1,4]-benzodiazepines (U.S. Pat. No. 4,192,803). On the basis of available literature, the 11H-1,2,4-triazolo[2,3-c][1,3]benzodiazepine ring system has not been described in the art.

SUMMARY OF THE INVENTION

The present invention concerns and has for its object the novel 5-diazacycloalkyl-1,2,4-triazolo[2,3-c][1,3]benzodiazepines and derivatives thereof. The invention also relates to processes for preparing said compounds, pharmaceutical compositions comprising said compounds, and application of said products in the treatment or management of psychoses (e.g. aggression, agitation) and/or allergy when administered, alone or in combination, to mammals.

The compounds of formula I exhibit valuable pharmacological properties, e.g. antihistaminic and psychotherapeutic e.g. antipsychotic (neuroleptic) effects. Said compounds, being essentially free of extrapyramidal effects, represent a novel chemical class of useful tranquilizers, primarily neuroleptic agents, essentially devoid of side effects e.g. dyskinesia and catalepsy seen with the classical major tranquilizers.

DETAILED DISCLOSURE OF THE INVENTION

Particularly the invention relates to compounds of formula I

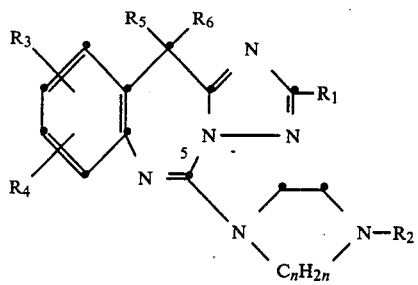

wherein $R_1$ is hydrogen, lower alkylthio, amino, (acyl, mono- or di-lower alkyl)-amino, lower alkoxy, acyloxy, lower alkyl, lower alkanoyl, hydroxy, halogen, trifluoromethyl, cyano, carboxy, lower alkoxycarbonyl, carbamoyl, mono- or di-lower alkyl-carbamoyl, hydroxy-lower alkyl or di-lower alkylamino-lower alkyl; $C_nH_{2n}$ is $C_2$-$C_4$-alkylene lower alkylene separating both nitrogen atoms by 2 or 3 carbon atoms; $R_2$ is hydrogen, lower alkyl, lower alkenyl, lower alkynyl, lower alkanoyl, aryl-lower alkyl, lower alkoxycarbonyl, lower phenylalkoxycarbonyl or (hydroxy, lower alkanoyloxy, aryloxy or lower alkoxy)-$C_2$-$C_7$-alkyl; $R_3$ and $R_4$ independently represent hydrogen, lower alkyl, lower alkoxy, lower alkylthio, halogen, trifluoromethyl, hydroxy, lower alkanoyloxy, sulfamoyl, mono- or di-lower alkylsulfamoyl; and $R_5$ and $R_6$ represent hydrogen or lower alkyl; the N-oxides; and pharmaceutically acceptable salts thereof.

Preferred embodiments of this invention relate to compounds of the formula I wherein $R_1$ is hydrogen, lower alkyl, halogen, trifluoromethyl, lower alkoxy or lower alkylthio; n represents the integer 2 to 4; $R_2$ is hydrogen, lower alkyl, lower alkoxycarbonyl or hydroxy-lower alkyl of 2 to 4 carbon atoms; $R_3$ represents hydrogen, lower alkyl, lower alkoxy, lower alkylthio, halogen or trifluoromethyl; $R_4$ represents hydrogen; and $R_5$ and $R_6$ represent hydrogen or lower alkyl; the N-oxides; and pharmaceutically acceptable salts thereof.

Highly preferred are compounds of the formula I wherein $R_1$ is hydrogen, methyl, ethyl, methylthio, chloro, methoxy or trifluoromethyl; n represents the integer 2 or 3; $R_2$ is hydrogen, alkyl of 1 to 3 carbon atoms, alkoxycarbonyl of 1 to 3 carbon atoms in the alkoxy portion, hydroxyethyl or hydroxypropyl; $R_3$ represents hydrogen, methyl, methoxy, methylthio, chloro or trifluoromethyl; $R_4$ represents hydrogen; $R_5$ and $R_6$ represent hydrogen or methyl; the N-oxides; and pharmaceutically acceptable salts thereof.

Especially preferred are the compounds of the formula II

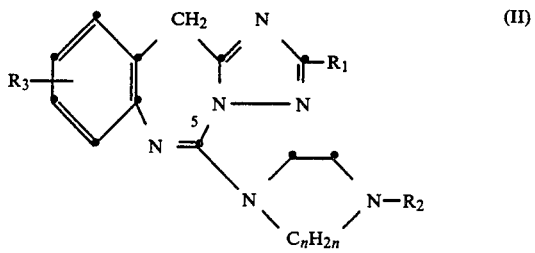

wherein $R_1$ represents hydrogen, halogen, trifluoromethyl, lower alkylmercapto, lower alkoxy or lower alkyl; $R_2$ represents hydrogen, lower alkyl or hydroxy-$C_2$-$C_7$-alkyl wherein the hydroxy group is separated from the nitrogen atom by at least 2 carbon atoms; $R_3$ represents hydrogen, lower alkyl, lower alkoxy, lower alkylthio, halogen or trifluoromethyl; $C_nH_{2n}$ represents ethylene or propylene; the N-oxides; and pharmaceutically acceptable salts thereof.

Further preferred are compounds of formula II wherein $R_1$ represents hydrogen, halogen, lower alkylthio, lower alkoxy or lower alkyl; $R_2$ represents hydrogen, lower alkyl or hydroxy-$C_2$-$C_4$-alkyl wherein the hydroxy group is separated from the nitrogen atom by 2 or 3 carbon atoms; $R_3$ represents hydrogen, lower alkyl, halogen or trifluoromethyl; and $C_nH_{2n}$ represents ethylene; and pharmaceutically acceptable salts thereof.

Of particular interest are compounds of formula II wherein $R_1$ represents hydrogen, methyl, ethyl, chloro, methylthio or methoxy; $R_2$ represents hydrogen, methyl, ethyl, propyl, 2-hydroxyethyl or 3-hydroxypropyl; $R_3$ is hydrogen, methyl, methoxy, fluoro, chloro or trifluoromethyl; and $C_nH_{2n}$ represents ethylene and pharmaceutically acceptable acid addition salts thereof.

The general definitions used herein have the meanings within the scope of the present invention as described below.

The term "lower" referred to above and hereinafter in connection with organic radicals or compounds respectively defines e.g. such alkyl, alkenyl or alkynyl radicals with up to and including 7, preferably up and including 4 and advantageously one or two carbon atoms.

Halogen is preferably fluoro or chloro, but may also be bromo or iodo.

A lower alkyl group or such present in said alkoxy, alkylthio or other alkylated groups, is above all methyl, but also ethyl, n- or i-(propyl, butyl, pentyl, hexyl or heptyl), e.g. 2-methylpropyl or 3-methylbutyl.

Lower alkenyl is preferably allyl.

Lower alkynyl is preferably propargyl.

Aryl-lower alkyl is preferably benzyl, 1-, 2- or 3-phenylpropyl, 1- or 2-phenylethyl, said radicals being optionally substituted on the phenyl ring preferably by e.g. halogen, lower alkoxy or lower alkyl.

A lower alkoxy group preferably contains 1 to 4 carbon atoms and represents for example ethoxy, propoxy, isopropoxy or advantageously methoxy.

A lower alkylthio group preferably contains 1 to 4 carbon atoms and represents for example ethylthio, propylthio or advantageously methylthio.

The term "acyl" represents lower alkanoyl, lower alkoxycarbonyl, carbamoyl, sulfamoyl, mono- or di-lower alkyl-(carbamoyl or sulfamoyl), halosulfonyl, lower phenylalkoxycarbonyl and the like.

Lower alkanoyl is preferably acetyl or propionyl. Lower alkanoyloxy is preferably acetyloxy or propionyloxy.

A lower alkoxycarbonyl, mono- or dialkyl-(carbamoyl or sulfamoyl) group is preferably ethoxycarbonyl, methoxycarbonyl; mono- or di-methyl(carbamoyl or sulfamoyl).

A lower phenylalkoxycarbonyl group represents preferably benzyloxycarbonyl.

A lower alkylene group $C_nH_{2n}$ is especially ethylene; but also 1,2- or 1,3-propylene, 1,2-, 1,3- or 2,3-butylene; thus forming with both adjacent nitrogen atoms a piperazinyl or homopiperazinyl moiety.

A $C_2$-$C_7$ hydroxyalkyl group is preferably 2-hydroxy-(ethyl or propyl), 3-hydroxy-(propyl or butyl) or 4-hydroxybutyl.

A lower alkanoyloxy-lower alkyl group represents preferably lower alkanoyloxy-(ethyl, propyl or butyl), e.g. 2-acetyloxy- or 2-propionyloxy-(ethyl, propyl or butyl), 3-acetyloxy- or 3-propionyloxy-(propyl or butyl), 4-acetyloxy- or 4-propionyloxybutyl and the like.

A lower alkyloxy-lower alkyl group represents preferably lower alkyloxy-(ethyl, propyl or butyl), e.g. 2-methoxy- or ethoxy-(ethyl, propyl or butyl), 3-methoxy- or 3-ethoxy-(propyl or butyl), 4-methoxy- or 4-ethoxybutyl and the like.

An aryloxy-lower alkyl group represents preferably phenyloxy-(ethyl, propyl or butyl), said radicals being optionally substituted on the phenyl ring preferably by e.g. halogen, lower alkoxy or lower alkyl.

Although N-oxides of compounds of formula I may represent such functionalized at one or more of any of the depicted ring nitrogen atoms in formula I, said N-oxides of the compounds of formula I are preferably derived from those wherein $R_2$ is lower alkyl, aryllower alkyl, or (hydroxy, lower alkanoyloxy, aryloxy or lower alkoxy)lower alkyl having at least 2 carbon atoms and wherein only the nitrogen atom bearing said $R_2$ substituent is thus functionalized.

Said compounds of formula I form acid addition salts, which are preferably such of pharmaceutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. acetic, propionic, succinic, glycolic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid.

Certain compounds of formula I, e.g. those with $R_1$ being carboxy also form pharmaceutically acceptable salts with bases which are preferably metal or ammonium salts, more particularly alkali or alkaline earth metal salts, e.g., the sodium, potassium, magnesium or calcium salt; or advantageously easily crystallizing ammonium salts derived from ammonia or organic amines, such as mono- di- or tri-lower (alkyl, cycloalkyl or hydroxyalkyl)amines, lower alkylenediamines or lower hydroxyalkylamines, cyclic amines or (aralkyl)alkylammonium bases, e.g., methylamine, diethylamine, triethylamine, dicyclohexylamine, triethanolamine, ethylenediamine, tris-(hydroxymethyl)-methylamine, piperidine, morpholine or benzyltrimethylammonium hydroxide.

The compounds of the invention exhibit valuable pharmacological properties, psychoactive, e.g. neuroleptic, as well as antiallergic e.g. antihistaminic effects. Such are demonstrable in animal tests using advantageously mammals, e.g. mice, rats, guinea pigs or monkeys, as test objects. Said compounds can be applied to them enterally or parenterally, advantageously orally, or subcutaneously, intravenously or intraperitoneally, for example, within gelatin capsules or in the form of starchy suspensions or aqueous solutions respectively.

The applied dosage may range between about 0.1 and 50 mg/kg/day, preferably between about 0.3 and 30 mg/kg/day, advantageously between about 1 and 20 mg/kg/day.

Said neuroleptic properties can be demonstrated in adult rats or squirrel monkeys, which are trained to press a lever to avoid the onset of an electric foot shock. Each lever press postpones the shock for 30 seconds. Whenever the animal fails to press the lever once within said period, brief (0.5 sec.) shocks are delivered at 15 second intervals until the animal again presses the lever. Under control conditions the animals press the lever at a moderately steady rate and seldom receive more than five or six shocks during a 25-minute (rats) and up to 4-hour experimental session. Said compounds evaluated for neuroleptic activity, are administered to the animals 30, 90, 210 minutes prior to the experimental session and block the learned conditioned avoidance behaviour, manifested by a decrease in avoidance responding with a marked increase in shocks taken by the animal. Both the avoidance responses and failures (shocks received) are recorded separately for evaluation.

Finally, said antihistaminic properties can be shown in vitro, e.g., according to Chasin et al., J. Neurochem. 22, 1031 (1974). Vesicles from a cell free preparation of guinea pig cerebral cortex are preincubated with $^3$H-adenine to form endogenous $^3$H-adenosine triphosphate. The vesicles are then incubated with 50 micromolar histamine to activate $^3$H-cyclic adenosine monophosphate synthesis in the absence or presence of the test compound at a concentration between 0.01 and 100 micromolar. When said compound is active, it inhibits the histamine activation of adenylate cyclase. The $IC_{50}$ represents the concentration at which histamine activation is inhibited by 50%.

Indicative of the antipsychotic utility of the compounds of this invention, e.g. the compound of example 1, namely 2-methyl-5-(4-methyl-1-piperazinyl)-11H-1,2,4-triazolo[2,3-c][1,3]benzodiazepine maleate, disrupts avoidance behaviour, e.g. decreases avoidance responses in rats and monkeys at an oral dose of about 1.0 mg/kg or lower.

Furthermore, the compound of example 1, an illustrative example of this invention, is essentially free of extrapyramidal side effects, e.g. dyskinesias and dystonias in the monkey at effective antipsychotic doses.

Illustrative of the antihistaminic activity, 2-methyl-5-(4-methyl-1-piperazinyl)-11H-1,2,4-triazolo[2,3-c][1,3]benzodiazepine maleate, the compound of example 1, inhibits histamine activation of adenylate cyclase, with an $IC_{50}$ of about $3 \times 10^{-7}M$.

Accordingly, the compounds of the invention are useful neuroleptic and antihistaminic agents, for example, in the treatment or management of psychotic manifestations, e.g., aggression, agitation, schizophrenia, and/or allergic conditions in mammals, including man. They are also useful intermediates in the preparation of other valuable products, especially of pharmacologically active compositions.

The compounds of the invention are prepared e.g. according to the following method, which comprises: condensing a compound of the formula III

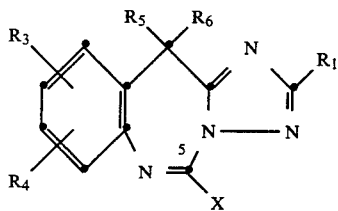

wherein X is a leaving group, preferably etherified mercapto, functionally modified hydroxy, cyanato or thiocyanato; and the remaining symbols have meaning as defined above for compounds of formula I; with a compound of formula IV

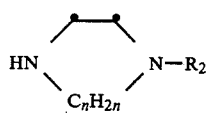

or an alkali metal derivative thereof wherein $R_2$ has meaning as defined above for compounds of formula I; and, if desired converting any resulting compound into another compound of the invention.

An etherified mercapto group is especially a mercapto group etherified by an optionally substituted hydrocarbon, particularly one of aliphatic character. It is especially lower alkylthio, for example methylthio, ethylthio or butylthio, or phenyl-lower-alkylthio, for example benzylthio, or phenylthio. A functionally modified reactive hydroxy group is for example, an etherified or esterified hydroxy group, for example halogen, such as chloro or bromo, lower alkylsulfonyloxy, such as methanesulfonyloxy, lower alkoxy such as methoxy or ethoxy, or di(lower alkoxy)-phosphonyloxy such as diethoxyphosphonyloxy.

Preferred are the intermediates of formula III wherein X represents halogen, lower alkoxy, lower alkylthio or cyanothio.

Said condensation is advantageously carried out with an excess of the compound IV, or with equivalent amounts of said metal derivatives prepared in situ therefrom preferably when X in formula III is halogen, lower alkylthio or cyanothio, advantageously and depending on the nature of said X, at temperatures between about 0° C. and 150°, and preferably in an appropriate solvent e.g. a lower alkanol such as amyl alcohol, dimethylformamide, hexamethylphosphoramide or toluene. Said condensation of a compound of formula III with a compound of formula IV may also be carried out in the presence of an acid, e.g., a hydrohalic acid such as hydrochloric acid.

The novel 11H-1,2,4-triazolo[2,3-c][1,3]benzodiazepine intermediates of formula III, e.g. wherein X is hydroxy or sulfhydryl are prepared according to ring closure procedures known per se, advantageously by condensing compounds of formula V

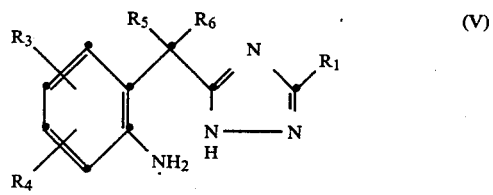

wherein $R_1$ and $R_3$–$R_6$ have meaning as previously defined for compounds of formula I, with reactive carbonic acid derivatives such as phosgene, thiophosgene, 1,1'-carbonyldiimidazole, cyanogen bromide and phenyl chloroformate.

Compounds of formula III wherein X is hydroxy can be converted to compounds wherein X is sulfhydryl by conventional sulfurating agents, such as phosphorus pentasulfide.

Compounds of formula III, e.g. wherein X is hydroxy or sulfhydryl, can be further derivatized to compounds of formula III above wherein X has the meaning given above, according to methods known per se or analogous to the procedures illustrated by the examples herein.

Starting materials of formula V are preferably prepared by reduction of the corresponding variously substituted 5-(o-nitrobenzyl)-1,2,4-triazoles, which are in turn preferably prepared by condensation of the correspondingly substituted o-nitrobenzylnitriles and lower alkyl imino ethers derived therefrom, with the hydrazides of the formula $R_1$—$CONHNH_2$ wherein $R_1$ has the meaning as defined above for compounds of formula I, by known methods illustrated in the examples herein.

The compounds of the invention are also advantageously prepared according to the following process comprising:
cyclizing a compound of formula VI

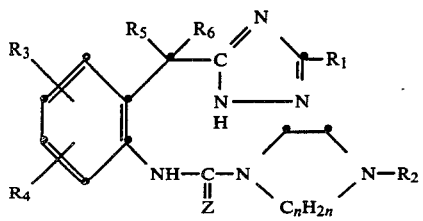

(VI)

wherein Z is oxygen, sulfur, or NH, and the other symbols have the above-given meaning, under dehydrating, dehydrosulfurating or deamination conditions; and if desired converting any resulting compound into another compound of the invention.

Said cyclization is preferably carried out at temperatures between 0° and 120° and advantageously in an inert solvent, such as acetonitrile and toluene, with reagents such as phosphorous halides and/or oxyhalides e.g. phosphorous pentachloride or phosphorous oxychloride, or cyanogen halides e.g. cyanogen bromide, with or without crown ether catalysts, such as 18-crown-6-ether, and with or without basic catalysts such as triethylamine or potassium carbonate.

The starting materials of formula VI can be obtained from precursors of formula III or tautomers thereof, wherein X is hydroxy, thio or amino by condensing them with compounds of formula IV in the presence or absence of other bases, e.g. those listed above, preferably in an inert solvent, such as methylene chloride or toluene at temperatures between 0° and 150°, advantageously between 10° and 50°. The ring opening reaction is preferably carried out at low temperature to minimize side reactions when $R_1$-$R_4$ represent reactive functional groups.

Alternately, starting materials of formula VI, wherein $R_2$ is lower alkanoyl, lower alkoxycarbonyl or phenyl-lower-alkoxycarbonyl, are prepared by condensing a compound of formula V above with a compound of formula VII

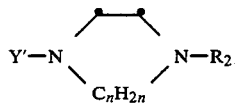

(VII)

wherein Y' represents halocarbonyl, halothiocarbonyl or cyano, and $R_2$ represents lower alkanoyl, lower alkoxycarbonyl or phenyl-lower alkoxycarbonyl, preferably in an inert solvent, at temperatures between about 0° and 150°, with or without basic catalysts such as triethylamine or potassium carbonate.

Starting materials of formula VII are preferably obtained by reacting compounds of formula IV wherein $R_2$ represents lower alkanoyl, lower alkoxycarbonyl or lower phenylalkoxycarbonyl, or advantageously e.g. the N-trimethylsilyl derivative thereof, with e.g. phosgene, thiophosgene or cyanogen bromide in an inert solvent such as ethyl ether, methylene chloride or dimethoxyethane at temperatures of about −70° to +50° with or without basic catalysts such as triethylamine or potassium carbonate.

The compounds of the invention so obtained can be converted into other compounds of formula I according to known methods. Thus, for example, those with $R_2$ being hydrogen or alkali metal, e.g., sodium or lithium salts thereof, can be reacted with substituted or unsubstituted oxiranes, such as ethylene oxide, or reactive esters of unsubstituted or correspondingly substituted aliphatic or araliphatic alcohols such as methanol, ethanol, methoxyethanol, phenoxyethanol, allyl alcohol, propargyl alcohol, e.g. such esterified by a strong inorganic or organic acid, above all hydrohalic acids, e.g. hydrochloric, hydrobromic or hydriodic acid; sulfuric or an aromatic sulfonic acid, e.g. p-toluene- or m-bromobenzene-sulfonic acid, in order to obtain the corresponding N-substituted compounds. Alkali metal intermediates of the compounds of formula I wherein $R_2$ is hydrogen and of the compounds of formula IV are obtained by metallation with reactive organometallic agents such as lithium diisopropylamide, with alkali metal alkoxides such as sodium methoxide, or alkali metal hydrides such as sodium or potassium hydride.

Unsaturated compounds, such as those with $R_2$ being lower alkenyl, lower alkynyl may be hydrogenated with catalytically activated hydrogen to obtain compounds wherein $R_2$ is the corresponding lower alkyl. Conversely, resulting N-alkylated compounds can be converted into N-unsubstituted compounds, e.g. by catalytic hydrogenolysis of N-benzyl compounds, or reaction of N-lower alkyl derivatives with lower alkyl haloformates, e.g. ethyl chloroformate, to yield N-acyl derivatives which, in turn, may be hydrolyzed to said unsubstituted compounds, those with $R_2$=H, for example with aqueous bases, such as alkali metal hydroxides, e.g. aqueous sodium hydroxide solution.

Compounds of formula I wherein $R_2$ is hydroxy-lower alkyl can also be prepared by first reacting corresponding compounds of formula I, wherein $R_2$ represents hydrogen, with reactive derivatives of corresponding glycols, glycolic acids or dicarboxylic acids, such as lower alkyl esters, halides or anhydrides thereof, or reactive esters of said glycols or glycolic acid derivatives, for example with hydrohalic or aromatic sulfonic acids, 1,2-dibromoethane or -propane, ethyl bromoacetate or -propionate, ethyl tosyloxyacetate, diethyl oxalate or malonate or ethyl oxalyl chloride. The intermediates so obtained are either hydrolyzed or reduced with simple or complex light metal hydrides such as lithium aluminum hydride, alone or with diborane to compounds of formula I wherein $R_2$ is hydroxyalkyl.

Compounds of formula I wherein $R_2$ is lower alkyl, e.g. methyl can be prepared by reacting the corresponding compounds of formula I wherein $R_2$ represents hydrogen with lower alkyl or phenyl lower alkyl haloformates, such as ethyl chloroformate, to obtain compounds of formula I wherein $R_2$ is lower alkoxycarbonyl or lower phenylalkyloxycarbonyl, and reducing said acyl derivatives with simple or complex light metal hydrides such as lithium aluminum hydride, sodium bis-(2-methoxy-ethoxy)-aluminum hydride, or sodium tri-t-butoxy-aluminum hydride.

N-acylated derivatives of formula I wherein $R_2$ is lower alkanoyl can preferably be obtained from compounds of formula I with $R_2$ being hydrogen and corresponding reactive carboxylic acid derivatives, e.g., halides, simple or activated esters, such as alkyl or cyanoalkyl esters or anhydrides. These in turn can be reduced as above to the compounds of formula I wherein $R_2$ is lower alkyl. Compounds of formula I wherein $R_2$ is hydroxy-lower alkyl may be acylated as above to the compounds wherein $R_2$ is lower alkanoyloxy-lower alkyl.

Compounds of formula I with $R_1$ being hydrogen, may be converted to the corresponding compounds with $R_1$ being halogen or acyl, e.g. by halogenation, preferably with chlorine in acetic acid or by acylation under Friedel-Crafts conditions with e.g. a lower alkanoyl halide, a lower alkyl haloformate or a trihaloacetyl halide optionally followed by treatment with an alkali metal lower alkoxide, hydroxide or amide. Any resulting carboxylic acid derivatives may then be hydrolyzed in known fashion, preferably under alkaline conditions and/or amidized with ammonia, mono- or di-lower alkylamines; the resulting primary carboxamides may in turn be dehydrated to the corresponding nitriles according to conventional methods.

Compounds of the formula I in which $R_1$ represents carboxy, can be prepared, for example, by hydrolysis of compounds wherein $R_1$ represents cyano, lower alkoxycarbonyl or carbamoyl.

Tertiary amines in which $R_2$ differs from hydrogen and is e.g. lower alkyl, aryl lower alkyl, can be converted into the N-oxides, for example with hydrogen peroxide or organic peracids, such as lower peralkanoic or perbenzoic acids, e.g. peracetic or m-chloroperbenzoic acid, advantageously at temperatures at or below room temperature with the latter, or up to 100° with hydrogen peroxide in the presence of lower alkanoic acids, e.g. acetic acid.

In any of the above processes, any interfering reactive functional group, e.g. hydroxy, amino, carboxy in any of the starting materials or intermediates may be temporarily protected by methods well known to the art.

Finally, the compounds of the invention are either obtained in the free form, or as a salt thereof. Any resulting base can be converted into a corresponding acid addition salt, preferably with the use of acids which yield a pharmaceutically acceptable salt, or with an anion exchange preparation, or any resulting salt can be converted into the corresponding free base, for example, with the use of a stronger base, such as a metal or ammonium hydroxide or a basic salt, e.g. an alkali metal hydroxide or carbonate, or a cation exchange preparation. Said acid addition salt are preferably such of pharmaceutically acceptable inorganic or organic acids described previously.

Compounds of formula I with $R_1$ being carboxy can be converted into the corresponding metal or ammonium salts by e.g. treatment with the alkaline or alkaline earth metal hydroxides or carbonates, ammonia or the amines listed previously.

These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compound is referred to in this context, a corresponding salt is also intended, provided such is possible or appropriate under the circumstances.

In case mixtures of geometrical or optical isomers of the above compounds, e.g. I to VII are obtained, these can be separated into the single isomers by methods in themselves known, e.g. by fractional distillation, crystallization and/or chromatography. Racemic products can likewise be resolved into the antipodes, for example, by separation of diastereomeric salts thereof, e.g. by the fractional crystallization of the salts formed with e.g. d- or l-tartaric acid, mandelic acid, cinchonidine and dehydroabietylamine.

The above-mentioned reactions are carried out according to standard methods, in the presence or absence of diluents, preferably such as are inert to the reagents and are solvents thereof, of catalysts, condensing or said other agents respectively and/or inert atmospheres, at low tempertures, room temperature or elevated temperatures, preferably at the boiling point of the solvents used, at atmospheric or superatmospheric pressure.

The invention further includes any variant of the present process, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reaction, that lead to the formation of those compounds, indicated above as being especially valuable, e.g. those of formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg weight may contain between about 10 and 100 mg of the active ingredient.

The following examples are intended to illustrate the invention and are not to be construed as being limitations thereon. Temperatures are given in degrees Centigrade, and all parts whereever given are parts by weight. If not mentioned otherwise, all evaporations are performed under reduced pressure, preferably between about 15 and 100 mm Hg. Proportions whereever given for liquids are in parts by volume.

EXAMPLE 1

A mixture of 6.94 g of 1-{o-[5-methyl-3-(1,2,4-triazolyl)methyl]-phenylcarbamoyl}-4-methylpiperazine, 52 ml of phosphorus oxychloride and 4.65 g of phosphorus pentachloride is stirred at room temperature for 5 hours and evaporated to dryness. The residue is suspended in 125 ml of methylene chloride, the mixture is cooled to 0° and 15.5 ml of triethylamine is added dropwise. The mixture is stirred at room temperature for 30 minutes and washed with cold water. The aqueous layer is in turn washed with methylene chloride and the combined organic layers are washed with water, dried over magnesium sulfate, decolorized with charcoal and evaporated. The residue is chromatographed with 50 g of silica gel using methylene chloride-methanol-ammonium hydroxide (450:50:1) as eluent to give as the less polar component 2-methyl-5-(4-methyl-1-piperazinyl)-11H-1,2,4-triazolo-[2,3-c][1,3]benzodiazepine.

A solution of 2-methyl-5-(4-methyl-1-piperazinyl)-11H-1,2,4-triazolo-[2,3-c][1,3]benzodiazepine in isopropanol is treated with a solution of an equimolar quantity of maleic acid in isopropanol to give 2-methyl-5-(4-methyl-1-piperazinyl)-11H-1,2,4-triazolo[2,3-c][1,3]-benzodiazepine monomaleate, m.p. 206°-208°, representing a salt of the compound of formula I wherein $R_1$ and $R_2=CH_3$, $R_3-R_6=H$ and $C_nH_{2n}=CH_2CH_2$.

The starting material is prepared as follows:

Absolute ethanol (2,250 ml) and 1,500 g (9.25 moles) of o-nitrophenylacetonitrile is charged into a 22 liter flask. The suspension is cooled to 5°-10° and hydrogen chloride is bubbled into the mixture for 2.5 hours. The reaction mixture is stirred at 10° under nitrogen atmosphere overnight. It is then diluted with 16,000 ml of ether and stirred for 1 hour; the solid is collected by filtration, washed with 4×1,000 ml of ether and dried (5 mm Hg/40°) to give ethyl 2-(o-nitrophenyl)-acetimidate hydrochloride, m.p. 122°-123° (dec).

To a solution of 4.1 g of ethyl 2-(o-nitrophenyl)-acetimidate hydrochloride in 40 ml of ethanol is added at room temperature and over a period of 10 minute, a solution of sodium ethoxide prepared by dissolving 0.38 g of sodium in 40 ml of ethanol. The mixture is stirred for 10 minutes and filtered. Acetylhydrazide (1.29 g) is added to the filtrate, the mixture is stirred at room temperature for 2 hours, the solids are filtered off and washed with ethanol to give N-acetyl-o-nitrophenylacetamidrazone, m.p. 195°-197°.

A mixture of 1.29 g of N-acetyl-o-nitrophenylacetamidrazone and 20 ml of ethanol is refluxed for 60 hours and evaporated to dryness. The oily residue is crystallized from ether to give 5-methyl-3-o-nitrobenzyl)-1,2,4-triazole, m.p. 119°-123°.

A mixture of 1.67 g of 5-methyl-3-(o-nitrobenzyl)-1,2,4-triazole, 42 mg of 10% palladium on charcoal and 15 ml of ethanol is hydrogenated at 3 atmospheres pressure for 4 hours, filtered, decolorized, evaporated to a small volume and diluted with ether to give 3-(o-aminobenzyl)-5-methyl-1,2,4-triazole, m.p. 143°-145°.

A mixture of 12.87 g of 3-(o-aminobenzyl)-5-methyl-1,2,4-triazole, 11.21 g of 1,1'-carbonylidiimidazole and 470 ml of methylene chloride is stirred at room temperature for 5 days and filtered. The filtrates are washed with water, dried over magnesium sulfate, decolorized, evaporated. The residue is recrystallized from tetrahydrofuran to give 2-methyl-11H-1,2,4-triazolo[2,3-c][1,3]benzodizepine-5-(6H)-one, m.p. 245°-247°, the intermediate of formula III wherein $X=OH$, $R_3-R_6=H$, $R_1=CH_3$ and $C_nH_{2n}=CH_2CH_2$.

A mixture of 7.23 g of 2-methyl-11H-1,2,4-triazolo[2,3-c][1,3]benzodiazepine-5(6H)-one, 5.45 g of N-methylpiperazine and 76 ml of methylene chloride is refluxed for 48 hours and evaporated to dryness. The residue is chromatographed with silica gel using methylene chloride-methanol-ammonium hydroxide (150:50:1) as eluent to give 1-{o[5-methyl-3-(1,2,4-triazolyl)methyl]-phenylcarbamoyl}-4-methylpiperazine as a foamy material; mass spectrum: $M^+/e=314$; the intermediate of formula VI wherein $C_nH_{2n}=CH_2CH_2$, $R_1$ and $R_2=CH_3$, $R_3-R_6=H$, and $Z=O$.

EXAMPLE 2

Prepared similarly according to the process of example 1 are the following compounds of formula I wherein $C_nH_{2n}$ is ethylene, $R_2$ is methyl and $R_4-R_6$ are hydrogen.

| Compound | $R_1$ | $R_3$ | Salt | m.p |
|---|---|---|---|---|
| 1 | $CH_2CH_3$ | H | maleate | 196-199° |
| 2 | H | H | maleate | 202-204° |
| 3 | H | 8-Cl | maleate | 215-217° |
| 4 | Cl | H | maleate | 216-218° |
| 5 | $SCH_3$ | H | maleate | 209-212° |
| 6 | $COOCH_2CH_3$ | H | | |

Intermediates of formula VI wherein $C_nH_{2n}$ is ethylene, $R_2$ is methyl, $R_4$ to $R_6$ are hydrogen and Z is oxo, for compounds 1 to 6 of formula I:

| Intermediate | $R_1$ | $R_3$ | m.p. | Remarks |
|---|---|---|---|---|
| 1/a | $CH_2CH_3$ | H | 153-159° | |
| 2/a | H | H | 205-208° | |
| 3/a | H | Cl | 182-186° | |
| 4/a | Cl | H | 190-195° | Cl para to triazolylmethyl group |
| 5/a | $SCH_3$ | H | 177-180° | |
| 6/a | $COOCH_2CH_3$ | H | | |

Intermediates of formula III wherein X represents OH and $R_4$ to $R_6$ are hydrogen, for compounds 1 to 6 of formula I:

| Intermediate | $R_1$ | $R_3$ | m.p. |
|---|---|---|---|
| 1/b | $CH_2CH_3$ | H | 165-178° |
| 2/b | H | H | 133-136° |
| 3/b | H | 8-Cl | 252-254° |
| 4/b | Cl | H | |
| 5/b | $SCH_3$ | H | 250-252° |
| 6/b | $COOCH_2CH_3$ | H | 216-220° |

Intermediates for compound 1

(a) N-propionyl-o-nitrophenylacetamidrazone, m.p. 184.5°-186.5°.

(b) 5-ethyl-3-(o-nitrobenzyl)-1,2,4-triazole, m.p. 100°-103°.

(c) 5-ethyl-3-(o-aminobenzyl)-1,2,4-triazole, m.p. 148.5°-151.5°.

Intermediate for compound 2

(a) N-formyl-o-nitrophenylacetamidrazone, m.p. 149°-151°, starting with formylhydrazide.

(b) 3-(o-nitrobenzyl)-1,2,4-triazole, m.p. 123°-125°.

(c) To a solution of 9.64 g of 3-(o-nitrobenzyl)-1,2,4-triazole in 150 ml of tetrahydrofurane, 220 ml of 1.3M aqueous solution of titanium trichloride is added and the mixture is stirred at room temperature for 24 hours. The mixture is cooled in an ice-water bath and concentrated ammonium hydroxide is added dropwise to bring the pH of the solution to 8; the solution is diluted further with water and extracted 4 times with methylene chloride. The combined extracts are decolorized with charcoal, dried over magnesium sulfate, evaporated to a small volume and diluted with ether to give 3-(o-aminobenzyl)-1,2,4-triazole, m.p. 134°–136°.

Intermediates for compound 3

(a) N-formyl-p-chloro-o-nitrophenylacetamidrazone, m.p. 173°–175° dec.
(b) 3-(p-chloro-o-nitrobenzyl)-1,2,4-triazole, m.p. 180°–185°.
(c) 3-(p-chloro-o-aminobenzyl)-1,2,4-triazole, m.p. 149°–152°.

Intermediates for compound 4

(a) To a solution of 2.36 g of ethyl o-nitrophenylacetimidate in 23 ml of ethanol is added dropwise at 0° a solution of sodium ethoxide prepared by dissolving 0.22 g of sodium in 11 ml of ethanol. The mixture is stirred for 30 minutes, filtered and to the filtrate is added 1 g of ethyl hydrazinocarbonate. The mixture is stirred at room temperature for 60 hours, evaporated to a small volume and filtered to give N-ethoxycarbonyl-o-nitrophenylacetamidrazone, m.p. 183°–185°.
(b) A mixture of 1 g of N-ethoxycarbonyl-o-nitrophenylacetamidrazone and 10 ml of amyl alcohol is refluxed overnight, cooled and filtered to give 5-hydroxy-3-(o-nitrobenzyl)-1,2,4-triazole, m.p. 210°–212.5°.
(c) A mixture of 1 g of 5-hydroxy-3-(o-nitrobenzyl)-1,2,4-triazole, 10 ml of phosphorus oxychloride and 1.89 g of phosphorus pentachloride is stirred at 70° for 11 hours, then at room temperature over the weekend and evaporated to dryness. The residue is dissolved in water, the solution is basified with 10% aqueous potassium carbonate and extracted 3 times with ethyl acetate. The combined extracts are dried over magnesium sulfate, decolorized with charcoal and evaporated to dryness. The residue is chromatographed with 50 g of silica gel using methylene chloride-ethyl acetate (1:1) as eluent to give 5-chloro-3-(o-nitrobenzyl)-1,2,4-triazole, m.p. 160°–163°.
(d) To a solution of 6.27 g of 5-chloro-3-(o-nitrobenzyl)-1,2,4-triazole in 146 ml of tetrahydrofuran is added to 0° with stirring 146 ml of 20% aqueous solution of titanium trichloride. The mixture is stirred at room temperature overnight basified with concentrated ammonium hydroxide and extracted 3 times with methylene chloride. The combined extracts are dried, evaporated and the residue is crystallized from ether to give 3-(o-aminobenzyl)-5-chloro-1,2,4-triazole, m.p. 162°–165°.
(e) A mixture of 0.35 g of 3-(o-aminobenzyl)-5-chloro-1,2,4-triazole, 9 ml of methylene chloride and 0.284 g of 1,1'-carbonyldiimidazole is stirred at room temperature overnight. The mixture is evaporated to a small volume and diluted with ether to give 1-{o-[5-chloro-3-(1,2,4-triazolyl)methyl]-phenylcarbamoyl}-imidazole, m.p. 165°–167°.
(f) A mixture of 0.324 g of 1-{o-[5-chloro-3-(1,2,4-triazolyl)methyl]-phenylcarbamoyl}-imidazole, 3 ml of methylene chloride and 0.11 g of N-methylpiperazine is stirred at room temperature overnight. The mixture is washed with water, dried over magnesium sulfate and evaporated to give 1-{o-[5-chloro-3-(1,2,4-triazolyl)methyl]-phenylcarbamoyl}-4-methyl-piperazine, m.p. 190°–195° (intermediate 4/a).

Intermediates for compound 5

(a) To a solution of 4.1 g of ethyl 2-(o-nitrophenyl)acetimidate in 40 ml of ethanol a solution of sodium ethoxide (prepared by dissolving 0.38 g of sodium in 40 ml of ethanol) is added dropwise at 0°. After stirring at room temperature for 30 minutes, the solids are filtered off, the filtrate is evaporated to a volume of approximately 10 ml and diluted with 20 ml of dimethyl sulfoxide. To the resulting solution 1.52 g of thiosemicarbazide is added and the mixture is stirred at room temperature for 2 days. The solvent is evaporated in vacuo, the residue is treated with water and ethyl acetate, the aqueous layer is extracted once more with ethyl acetate and the combined organic extracts are washed with water, dried over magnesium sulfate, evaporated to a small volume and diluted with ether to give N-(aminothiocarbonyl)-o-nitrophenylacetamidrazone, m.p. 172°–174°.
(b) A mixture of 1 g of N-(aminothiocarbonyl)-o-nitrophenylacetamidrazone and 10 ml of amyl alcohol is refluxed for 6 hours, evaporated to a small volume and diluted with ether to give 5-mercapto-3-(o-nitrobenzyl)-1,2,4-triazole, m.p. 239°–241°.
(c) To a suspension of 0.61 g of sodium hydride in 50 ml of tetrahydrofuran, 5 g of 5-mercapto-3-(o-nitrobenzyl)-1,2,4-triazole is added in portions with stirring at room temperature over a period of 30 minutes. The mixture is stirred for 2 hours, 1.51 ml of methyl iodide is added at once, the mixture is stirred overnight at room temperature and evaporated to dryness in vacuo. The residue is treated with water and methylene chloride, the aqueous layer is extracted once more with methylene chloride, the combined organic extracts are dried over magnesium sulfate, evaporated to a small volume and diluted with ether to give 5-methylmercapto-3-(o-nitrobenzyl)-1,2,4-triazole, m.p. 120°–132°.
(d) To a solution of 2 g of 5-methylmercapto-3-(o-nitrobenzyl)-1,2,4-triazole in 45 ml of tetrahydrofuran is added 44 ml of 20% aqueous titanium trichloride dropwise at 0°. The mixture is stirred at room temperature overnight, diluted with water, cooled to 0°, basified with ammonium hydroxide and extracted three times with methylene chloride. The organic extracts are dried and evaporated and the residue is crystallized from toluene to give 3-(o-aminobenzyl)-5-methylmercapto-1,2,4-triazole, m.p. 99°–102°.
(e) A mixture of 7 g of 3-(o-aminobenzyl)-5-methylmercapto-1,2,4-triazole, 5.26 g of 1,1'-carbonyldiimidazole and 179 ml of methylene chloride is heated at reflux overnight. Most of the solvent is removed in vacuo, the solids are filtered and washed with small amount of methylene chloride to give 2-methylmercapto-11H-1,2,4-triazolo[2,3-c][1,3]benzodiazepine-5(6H)-one, m.p. 250°–252° (intermediate 5/b).

Intermediates for compound 6

(a) To a solution of 1.86 g of ethyl 2-(o-nitrophenyl)acetimidate in 19 ml of ethanol a solution of sodium ethoxide (prepared by dissolving 0.17 g of sodium in 8.7 ml of ethanol) is added dropwise at 0°. After stirring the mixture for 30 minutes, the solids are filtered off, 1 g of ethyl oxalyl hydrazide is added and the mixture is stirred at room temperature for 48 hours. The product is filtered off and washed with ethanol to give N-carboethoxycarbonyl-o-nitrophenylacetamidrazone, m.p. 136°–138°.

(b) A mixture of 23.97 g of N-carboethoxycarbonyl-o-nitrophenylacetamidrazone and 240 ml of ethanol is refluxed overnight, filtered and evaporated. The residue is chromatographed with silica gel using methylene chloride-methanol-ammonium hydroxide (300:50:1) as eluent to give 5-ethoxycarbonyl-3-(o-nitrobenzyl)-1,2,4-triazole, m.p. 135°–140°.

(c) A mixture of 1 g of 5-ethoxycarbonyl-3-(o-nitrobenzyl)-1,2,4-triazole, 10 ml of ethanol and 25 mg of platinum oxide is hydrogenated at 3 atmospheres pressure for 2 hours, filtered and evaporated to give 3-(o-aminobenzyl)-5-ethoxycarbonyl-1,2,4-triazole.

(d) A mixture of 13.96 g of 3-(o-aminobenzyl)-5-ethoxycarbonyl-1,2,4-triazole, 410 ml of methylene chloride and 9.19 g of 1,1'-carbonyldimidazole is stirred at room temperature for 2 days and filtered. The filtrate is washed with water, dried over magnesium sulfate, decolorized with charcoal, evaporated to a small volume and diluted with ether. The product is filtered off and recrystallized from tetrahydrofuran to give 2-ethoxycarbonyl-11H-1,2,4-triazolo[2,3-c][1,3]benzodiazepine-5(6H)-one, m.p. 216°–220° (intermediate 6/b).

EXAMPLE 3

To a solution of 6.25 g of 2-methyl-5-cyanothio-11H-1,2,4-triazolo[2,3-c][1,3]benzodiazepine in 7.3 ml of hexamethylphosphoramide is added dropwise, at 0°, 4.94 g of N-methylpiperazine over a period of 5 minutes. The mixture is stirred at room temperature for 4 hours, poured into water and extracted with ethyl acetate. The organic extracts are washed with water, dried over magnesium sulfate and evaporated to dryness to give 2-methyl-5-(4-methyl-1-piperazinyl)-11H-1,2,4-triazolo[2,3-c][1,3]benzodiazepine, m.p. 185°–187°. This material is treated with an equivalent amount of maleic acid to give 2-methyl-5-(4-methyl-1-piperazinyl)-11H-1,2,4-triazolo[2,3-c][1,3]benzodiazepine monomaleate of example 1.

The starting material is prepared as follows:

To a solution of 5.41 g of thiophosgene in 30 ml of methylene chloride is added dropwise at 0° a solution of 7.5 g of 5-methyl-3-(o-aminobenzyl)-1,2,4-triazole and 8.07 g of triethylamine in 285 ml of methylene chloride over a period of 45 minutes. The mixture is stirred at room temperature overnight, washed first with 10% aqueous potassium bicarbonate, then with water, dried over magnesium sulfate, decolorized with charcoal and evaporated to dryness to give 5-methyl-3-(o-isothiocyanatobenzyl)-1,2,4-triazole; IR 2080 cm$^{-1}$.

To a suspension of 0.91 g of sodium hydride in 27 ml of tetrahydrofuran is added dropwise a solution of 8.74 g of 5-methyl-3-(o-isothiocyanatobenzyl)-1,2,4-triazole in 60 ml of tetrahydrofuran over a period of 20 minutes. The mixture is stirred at room temperature for 2 hours. To the resulting suspension a solution of 4.02 g of cyanogen bromide in 35 ml of tetrahydrofuran is added dropwise at 0° over a period of 15 minutes. The mixture is stirred at 0° for 1.5 hours, poured into water and extracted three times with ethyl acetate. The organic extracts are dried over magnesium sulfate, decolorized with charcoal and evaporated to give 2-methyl-5-cyanothio-11H-1,2,4-triazolo[2,3-c][1,3]benzodiazepine; IR 2150 cm$^{-1}$.

EXAMPLE 4

To a solution of 1.0 g of 2-methyl-5-(4-ethoxycarbonyl-1-piperazinyl)-11H-1,2,4-triazolo[2,3-c][1,3]benzodiazepine in 10 ml of dry tetrahydrofuran, 500 mg of lithium aluminum hydride are added at once and the mixture is refluxed under nitrogen for 24 hours. The mixture is cooled to 0°, the excess of the lithium aluminum hydride is destroyed with ethyl acetate, the mixture is then poured into water and extracted with ethyl acetate. The extracts are dried and evaporated to give after purification 2-methyl-5-(4-methyl-1-piperazinyl)-11H-1,2,4-triazolo[2,3-c][1,3]-benzodiazepine of example 1.

The starting material is prepared e.g. according to the procedure of example 3 by condensing 2-methyl-5-cyanothio-11H-1,2,4-triazolo[2,3-c][1,3]benzodiazepine with N-carboethoxypiperazine.

EXAMPLE 5

To a solution of 200 mg of 2-methyl-5-(4-benzyloxycarbonyl-1-piperazinyl)-11H-1,2,4-triazolo[2,3-c][1,3]benzodiazepine in 0.6 ml of acetic acid are added 0.70 ml of a 2N solution of hydrobromic acid in acetic acid. The mixture is heated at 100° for 2 hours and stirred at room temperature overnight. Workup yields 2-methyl-5-(4H-1-piperazinyl)-11H-1,2,4-triazolo[2,3-c][1,3]benzodiazepine.

The starting material is prepared similarly to starting material of example 4 by replacing 1-ethoxycarbonylpiperazine with the equivalent amount of 1-benzyloxycarbonylpiperazine.

EXAMPLE 6

A mixture of 300 mg of 5-(4H-1-piperazinyl)-11H-1,2,4-triazolo[2,3-c][1,3]benzodiazepine, 0.5 g of potassium carbonate, 1 mole equivalent of methyl iodide and 2 ml of acetone is stirred at room temperature overnight and evaporated. Water is added to the residue, and the mixture is extracted with methylene chloride. The extracts are dried over magnesium sulfate, evaporated, and the residue is purified to give 2-methyl-5-(4-methyl-1-piperazinyl)-11H-1,2,4-triazolo[2,3-c][1,3]benzodiazepine of example 1.

EXAMPLE 7

To a solution of 5 g of 2-methyl-5-(4-methyl-1-piperazinyl)-11H-1,2,4-triazolo[2,3-c][1,3]benzodiazepine in 50 ml of methylene chloride is added in portions 3.75 g of m-chloroperbenzoic acid with stirring at 0°. The mixture is then stirred at room temperature overnight and evaporated to dryness. The foamy residue is passed through 100 g of Amberlite IRA-400 ion exchange resin using water as eluent. Evaporation of the eluent gives 2-methyl-5-(4-methyl-4-oxido-1-piperazinyl)-11H-1,2,4-triazolo[2,3-c][1,3]benzodiazepine.

EXAMPLE 8

The following compounds are prepared according to the methods illustrated by the previous examples and are obtained from equivalent amounts of the correspondingly substituted starting materials.

(a)  2-methyl-5-(4-benzyl-1-piperazinyl)-11H-1,2,4-triazolo[2,3-c][1,3]-benzodiazepine;

(b) 2-methyl-5-(4-allyl-1-piperazinyl)-11H-1,2,4-triazolo[2,3-c][1,3]-benzodiazepine;
(c) 2-methyl-5-(4-methyl-1-homopiperazinyl)-11H-1,2,4-triazolo-[2,3-c][1,3]benzodiazepine;
(d) 2,8-dimethyl-5-(4-methyl-1-piperazinyl)-11H-1,2,4-triazolo-[2,3-c][1,3]benzodiazepine;
(e) 8-fluoro-2-methyl-5-(4-methyl-1-piperazinyl)-11H-1,2,4-triazolo-[2,3-c][1,3]benzodiazepine;
(f) 8-methoxy-2-methyl-5-(4-methyl-1-piperazinyl)-11H-1,2,4-triazolo[2,3-c][1,3]benzodiazepine;
(g) 2-methyl-5-(4-hydroxyethyl-1-piperazinyl)-11H-1,2,4-triazolo-[2,3-c][1,3]benzodiazepine.

EXAMPLE 9

Amyl alcohol (5100 ml) and 918.35 g of N-methylpiperazine are charged into a 12 liter 3-necked reaction flask fitted with Dean-Stark adapter. The solution is stirred under nitrogen atmosphere and 989 ml of 10N ethanolic hydrogen chloride solution are added rapidly. The reaction mixture is heated to reflux and the distillate is collected in the Dean-Stark adapter. When the temperature of the reaction mixture reaches 131°, the Dean-Stark adapter is removed and an additional 918.35 g of N-methylpiperazine followed by 1112.6 g of 2-methyl-5-methylthio-11H-1,2,4-triazolo[2,3-c][1,3]-benzodiazepine are added. The mixture is heated to reflux under nitrogen atmosphere for 20 hours. Amyl alcohol is then removed under reduced pressure at a water bath temperature of 80°. The viscous residual oil is dissolved in 10,000 ml of methylene chloride, washed with 3×4,000 ml of 4N sodium hydroxide and 6×4,000 ml of water. The methylene chloride solution is then extracted with 3×2,000 ml of 6N hydrochloric acid. The aqueous solution is washed with 2×2,000 ml of methylene chloride, decolorized with charcoal and filtered. The aqueous filtrate is adjusted to pH 9-10 with 1,500 ml of concentrated ammonium hydroxite solution. The separated oil is extracted with 3×4,000 ml of methylene chloride, the extracts are dried over 1000 g of sodium sulfate and the solvent is removed to give 2-methyl-5-(4-methyl-1-piperazinyl)-11H-1,2,4-triazolo[2,3-c]-[1,3]benzodiazepine of Example 1. Treatment with an equimolar amount of maleic acid in isopropanol yields 2-methyl-5-(4-methyl-1-piperazinyl)-11H-1,2,4-triazolo[2,3-c][1,3]benzodiazepine monomaleate of Example 1.

The starting material is prepared as follows:

To a suspension of 0.91 g of sodium hydride in 27 ml of tetrahydrofuran is added dropwise a solution of 8.74 g of 5-methyl-3-(o-isothiocyanatobenzyl)-1,2,4-triazole in 60 ml of tetrahydrofuran over a period of 20 minutes. The mixture is stirred at room temperature for 2 hours. To the resulting suspension is added a solution of 5.4 g of methyl iodide in 35 ml of tetrahydrofuran dropwise at 0° over a period of 15 minutes. The mixture is stirred at room temperature for 1 hour, poured into water and extracted three times with methylene chloride. The organic extracts are dried over magnesium sulfate, decolorized with charcoal and evaporated to give 2-methyl-5-methylthio-11H-1,2,4-triazolo[2,3-c][1,3]benzodiazepine.

2-Methyl-5-methylthio-11H-1,2,4-triazolo[2,3-c][1,3]benzodiazepine is also prepared as follows:

A suspension of 8 g of 5-methyl-3-(o-isothiocyanatobenzyl)-1,2,4-triazole in 100 ml of toluene is refluxed overnight and cooled to room temperature to give 2-methyl-11H-1,2,4-triazolo[2,3-c][1,3]-benzodiazepine-5(6H)-thione. Treatment with methyl iodide as described above yields 2-methyl-5-methylthio-11H-1,2,4-triazolo[2,3-c][1,3]benzodiazepine.

EXAMPLE 10

The following compounds of formula II are prepared according to the methods illustrated by the previous examples and are obtained from equivalent amounts of the corresponding substituted starting materials.

| No. | $R_1$ | $R_2$ | $R_3$ | $C_nH_{2n}$ |
| --- | --- | --- | --- | --- |
| 1 | $CH_3$ | $HOCH_2CH_2$ | H | $(CH_2)_2$ |
| 2 | $CH_3$ | $HOCH_2CH_2CH_2$ | H | $(CH_2)_2$ |
| 3 | H | $CH_3$ | 8-$CF_3$ | $(CH_2)_2$ |
| 4 | H | $CH_3$ | 8-F | $(CH_2)_2$ |
| 5 | H | $CH_3$ | 8-$OCH_3$ | $(CH_2)_2$ |
| 6 | H | $CH_3CH_2CH_2$ | H | $(CH_2)_2$ |
| 7 | $OCH_3$ | $CH_3$ | H | $(CH_2)_2$ |
| 8 | $CF_3$ | $CH_3$ | H | $(CH_2)_2$ |
| 9 | H | $CH_3$ | 8-$CH_3$ | $(CH_2)_2$ |

EXAMPLE 11

Preparation of 10,000 capsules each containing 10 mg of the active ingredient:

| Formula: | |
| --- | --- |
| 2-Methyl-5-(4-methyl-1-piperazinyl)-11H—1,2,4-triazolo[2,3-c][1,3]benzodiazepine monomaleate | 100.0 g |
| Lactose | 1,800.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

EXAMPLE 12

Preparation of 10,000 tablets each containing 25 mg of the active ingredient:

| Formula: | |
| --- | --- |
| 2-Methyl-5-(4-methyl-1-piperazinyl)-11H—1,2,4-triazolo[2,3-c][1,3]benzodiazepine monomaleate | 250.00 g |
| Lactose | 957.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water. The paste formed is added to the powders which are granulated, if necessary, with an additional amount of water. The granulate is dried overnight at 35° C., broken on a screen with 1.2 mm openings and compressed into tablets using concave punches with 6.4 mm diameter, uppers bisected.

Analogously tablets or capsules are prepared from the remaining compounds of the invention, e.g. those illustrated by the other examples herein.

What is claimed is:
1. A compound of the formula

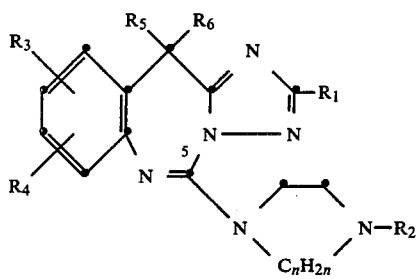

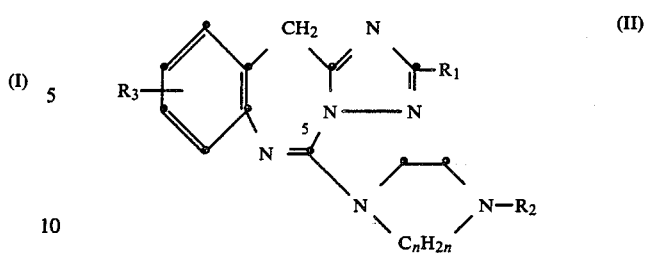

wherein $R_1$ is hydrogen, lower alkylthio, amino, (lower alkanoyl, mono- or di-lower alkyl)-amino, lower alkoxy, lower alkanoyloxy, lower alkyl, lower alkanoyl, hydroxy, halogen, trifluoromethyl, cyano, carboxy, lower alkoxycarbonyl, carbamoyl, mono- or di-lower alkyl-carbamoyl, hydroxy-lower alkyl or di-lower alkylamino-lower alkyl; $C_nH_{2n}$ is $C_2$–$C_4$-alkylene separating both nitrogen atoms by 2 or 3 carbon atoms thus forming with both adjacent nitrogen atoms a piperazinyl of homopiperazinyl moiety; $R_2$ is hydrogen, lower alkyl, lower alkenyl, lower alkynyl, lower alkanoyl, aryl-lower alkyl, lower alkoxycarbonyl, lower phenylalkoxycarbonyl or (hydroxy, lower alkanoyloxy, aryloxy or lower alkoxy)-$C_2$–$C_7$-alkyl; $R_3$ and $R_4$ independently represent hydrogen, lower alkyl, lower alkoxy, lower alkylthio, halogen, trifluoromethyl, hydroxy, lower alkanoyloxy, sulfamoyl, mono- or di-lower alkylsulfamoyl; and $R_5$ and $R_6$ represent hydrogen or lower alkyl; and wherein within the above definitions aryl represents phenyl or phenyl substituted by halogen, lower alkoxy or lower alkyl; an N-oxide; or a pharmaceuticaly acceptable salt thereof.

2. A compound according to claim 1 wherein $R_1$ is hydrogen, lower alkyl, halogen, trifluoromethyl, lower alkoxy or lower alkylthio; n represents the integer 2 to 4; $R_2$ is hydrogen, lower alkyl, lower alkoxycarbonyl or hydroxy-lower alkyl of 2 to 4 carbon atoms; $R_3$ represents hydrogen, lower alkyl, lower alkoxy, lower alkylthio, halogen or trifluoromethyl; $R_4$ represents hydrogen; and $R_5$ and $R_6$ represent hydrogen or lower alkyl; an N-oxide; or a pharmaceutically acceptable salt thereof.

3. A compound according to claim 1 wherein $R_1$ is hydrogen, methyl, ethyl, methylthio, chloro, methoxy or trifluoromethyl; n represents the integer 2 or 3; $R_2$ is hydrogen, alkyl of 1 to 3 carbon atoms, alkoxycarbonyl of 1 to 3 carbon atoms in the alkoxy portion, hydroxyethyl or hydroxypropyl; $R_3$ represents hydrogen, methyl, methoxy, methylthio, chloro or trifluoromethyl; $R_4$ represents hydrogen; $R_5$ and $R_6$ represents hydrogen or methyl; an N-oxide; or a pharmaceutically acceptable salt thereof.

4. A compound according to claim 1 having the formula wherein $R_1$ represents hydrogen, halogen, trifluoromethyl, lower alkylthio, lower alkoxy or lower alkyl; $R_2$ represents hydrogen, lower alkyl or hydroxy-$C_2$–$C_7$ alkyl wherein the hydroxy group is separated from the nitrogen atom by 2 to 7 carbon atoms; $R_3$ represents hydrogen, lower alkyl, lower alkoxy, lower alkylthio, halogen or trifluoromethyl; $C_nH_{2n}$ represents ethylene or propylene; an N-oxide; or a pharmaceutically acceptable salt thereof.

5. A compound according to claim 4 wherein $R_1$ represents hydrogen, halogen, lower alkylthio, lower alkoxy or lower alkyl; $R_2$ represents hydrogen, lower alkyl or hydroxy-$C_2$–$C_4$-alkyl wherein the hydroxy group is separated from the nitrogen atom by 2 or 3 carbon atoms; $R_3$ represents hydrogen, lower alkyl, halogen or trifluoromethyl; and $C_nH_{2n}$ represents ethylene; or a pharmaceutically acceptable salt thereof.

6. A compound according to claim 4 wherein $R_1$ represents hydrogen, methyl, ethyl, chloro, methylthio or methoxy; $R_2$ represents hydrogen, methyl, ethyl, propyl, 2-hydroxyethyl or 3-hydroxypropyl; $R_3$ is hydrogen, methyl, methoxy, fluoro, chloro or trifluoromethyl; and $C_nH_{2n}$ represents ethylene; or a pharmaceutically acceptable salt thereof.

7. A compound according to claim 4 being 2-methyl-5-(4-methyl-1-piperazinyl)-11H-1,2,4-triazolo[2,3-c][1,3]benzodiazepine or a pharmaceutically acceptable acid addition salt thereof.

8. A compound according to claim 4 being 2-chloro-5-(4-methyl-1-piperazinyl)-11H-1,2,4-triazolo[2,3-c][1,3]benzodiazepine or a pharmaceutically acceptable salt thereof.

9. A neuroleptic and pharmaceutical composition comprising an effective amount of a pharmacologically active compound as claimed in claim 1 in combination with one or more pharmaceutical carriers.

10. A method for the treatment or management of aggression, agitation, schizophrenia which comprises administering enterally or parenterally to a mammal suffering therefrom a pharmaceutical composition comprising an effective amount of a compound of claim 1 in combination with one or more pharmaceutical carriers.

11. A method for the treatment of aggression, agitation, in schizophrenia mammals which comprises administering to a mammal suffering therefrom a pharmaceutical composition comprising an effective amount of a compound of claim 7 in combination with one or more pharmaceutical carriers.

* * * * *